US010679725B2

(12) United States Patent
Hosseini et al.

(10) Patent No.: US 10,679,725 B2
(45) Date of Patent: Jun. 9, 2020

(54) PREDICTING SKIN AGE BASED ON THE ANALYSIS OF SKIN FLORA AND LIFESTYLE DATA

(71) Applicant: ProdermIQ, Inc., San Diego, CA (US)

(72) Inventors: Dana Hosseini, San Diego, CA (US); Sasan Amini, Redwood City, CA (US); Eveie Schwartz, San Diego, CA (US)

(73) Assignee: PRODERMIQ, INC., San Diego, CA (US)

(*) Notice: Subject to any disclaimer, the term of this patent is extended or adjusted under 35 U.S.C. 154(b) by 96 days.

(21) Appl. No.: 15/760,813

(22) PCT Filed: Sep. 16, 2016

(86) PCT No.: PCT/US2016/052161
§ 371 (c)(1),
(2) Date: Mar. 16, 2018

(87) PCT Pub. No.: WO2017/049103
PCT Pub. Date: Mar. 23, 2017

(65) Prior Publication Data
US 2018/0260514 A1   Sep. 13, 2018

Related U.S. Application Data

(60) Provisional application No. 62/220,072, filed on Sep. 17, 2015.

(51) Int. Cl.
| | | |
|---|---|---|
| *G16B 5/00* | (2019.01) | |
| *G16B 20/00* | (2019.01) | |
| *G16H 50/30* | (2018.01) | |
| *A61B 34/10* | (2016.01) | |
| *G16H 20/30* | (2018.01) | |
| *A61B 10/02* | (2006.01) | |
| *C12Q 1/689* | (2018.01) | |

(52) U.S. Cl.
CPC .............. *G16B 5/00* (2019.02); *A61B 10/02* (2013.01); *A61B 34/10* (2016.02); *C12Q 1/689* (2013.01); *G16B 20/00* (2019.02); *G16H 20/30* (2018.01); *G16H 50/30* (2018.01)

(58) Field of Classification Search
CPC .............. C12Q 1/689; C12Q 2600/106; C12Q 2600/112; C12Q 2600/118; C12Q 2600/158; C12Q 1/02; C12Q 1/6883; C12Q 2600/16; A61B 10/02; A61B 34/10; A61B 10/0038; A61B 10/04; A61B 2010/0061; A61B 5/4343; G01N 2570/00; G01N 2800/20; G01N 33/56911; G16B 20/00; G16B 5/00; G16B 25/10; G16B 30/00; G16B 40/00; G16H 20/30; G16H 50/30; A61K 35/741; A61K 35/76; A61K 39/0208; A61K 39/05; A61K 35/74; A61K 35/744; A61K 35/745; A61K 35/747; A61K 48/00; A61K 8/99; A61K 9/0014; C12N 2795/00032; C12N 7/00; C12N 1/00; C12N 1/20; G06N 20/00; A01N 63/00; A61L 15/36; A61Q 15/00; A61Q 17/04; A61Q 19/00; A61Q 19/02; A61Q 19/04; C07K 14/195; C12R 1/01
See application file for complete search history.

(56) References Cited

U.S. PATENT DOCUMENTS

| | | |
|---|---|---|
| 10,169,541 B2 | 1/2019 | Apte et al. |
| 10,354,756 B2 | 7/2019 | Apte et al. |
| 10,364,473 B2 | 7/2019 | Li et al. |
| 10,366,793 B2 | 7/2019 | Apte et al. |
| 10,381,112 B2 | 8/2019 | Apte et al. |
| 10,381,117 B2 | 8/2019 | Apte et al. |
| 10,395,777 B2 | 8/2019 | Apte et al. |
| 10,410,749 B2 | 9/2019 | Apte et al. |
| 2009/0035329 A1* | 2/2009 | Blaser .................. A61K 35/74 424/234.1 |
| 2015/0259728 A1 | 9/2015 | Cutliffe et al. |
| 2016/0215326 A1 | 7/2016 | Martin et al. |
| 2017/0344719 A1 | 11/2017 | Apte et al. |
| 2018/0030516 A1 | 2/2018 | Nawana et al. |
| 2018/0137243 A1 | 5/2018 | Belnap |
| 2019/0050534 A1 | 2/2019 | Apte et al. |
| 2019/0213226 A1 | 7/2019 | Ludwinski et al. |
| 2019/0237194 A1 | 8/2019 | Salvi et al. |

FOREIGN PATENT DOCUMENTS

| | | |
|---|---|---|
| WO | WO-2014205088 A2 | 12/2014 |
| WO | WO-2015076617 A1 | 5/2015 |

OTHER PUBLICATIONS

Baehrecke, EH. Autophagic programmed cell death in *Drosophila*. Cell Death Differ. 10(9):940-945 (Sep. 2003).
Brennecke et al. Bantam encodes a developmentally regulate microRNA that control cell proliferation and regulates the proapoptotic gene hid in *Drosophila*. Cell 113(1):25-36 (2003).
Lee, R.C. et al. The C. elegans heterochronic gene lin-4 encodes small RNAs with antisense complementarity to lin-14. Cell, 75(5):843-854 (Dec. 3, 1993).
Reinhart et al. The 21-nucleotide let-7 RNA regulates developmental timing in Caenorhabditis elegans, Nature,. 403:901-906, 2000.
Bartel, DP.MicroRNAs: genomics, biogenesis, mechanism, and function.Cell. 116(2):281-97 (Jan. 23, 20043).
Yi et al. Morphogenesis in skin is governed by discrete sets of differentially expressed microRNAs. Nature Genetics 38(3):356-362 (2006).

(Continued)

*Primary Examiner* — Deborah K Ware
(74) *Attorney, Agent, or Firm* — Wilson Sonsini Goodrich & Rosati (57) ABSTRACT

The present invention relates to a combination of experimental and computational workflows that allow characterization of specific molecular mechanisms by which the microbiome contribute to skin health and skin age.

12 Claims, 6 Drawing Sheets

(56) References Cited

OTHER PUBLICATIONS

EP16847400.5 Extended Search Report dated Apr. 29, 2019.
Grice et al. The skin mirobiome. Nat Rev Microbiol 9(4):244-253 (2011).
Leyden et al. Age-related changes in the resident bacterial flora of the human face. J Invest Dermatol 65(4):379-81 (1975).

\* cited by examiner

PREDICTING SKIN AGE BASED ON THE ANALYSIS OF SKIN FLORA AND LIFESTYLE DATA

RELATED APPLICATION DATA

This application claims the benefit of priority under 35 U.S.C. § 119(e) of U.S. Provisional Patent Application Ser. No. 62/220,072, filed Sep. 17, 2015, the entire contents of which is incorporated herein by reference in its entirety.

BACKGROUND OF THE INVENTION

Field of the Invention

The invention relates generally to computational methods and more specifically to methods and a system for characterizing skin age as a function of skin flora.

Background Information

About 100 trillion microorganisms live in and on the human body vastly outnumbering the body's approximately 10 trillion human cells. These normally harmless viruses, bacteria and fungi are referred to as commensal or mutualistic organisms. Commensal and mutualistic organisms help keep our bodies healthy in many ways: they help us to digest foods and acquire nutrients such as vitamins B and K, encourage the immune system to develop and prevent the colonization of, for example, bacterial pathogens that cause disease by competing with them. Together all of the microorganisms living in and on the body—commensal, mutualistic and pathogenic—are referred to as the microbiome and their equilibrium and associated metabolome is closely linked to an individual's health status and vice-versa.

Next generation sequencing (NGS) has created an opportunity to quickly and accurately identify and profile the microbiome inhabiting the skin and subcutaneous tissue. The optimal flora also interacts with the host immune system in a synergistic way further propagating its health benefits. The associated metabolome of individuals can also be profiled either by a mass-spectrometry based system or using genomics-based metabolome modeling and flux-balance analysis and used to make a healthy metabolome profile. All these methodologies can be used to dissect the complexity of microbial communities.

The highly dynamic microbial communities than live on the skin are important to skin health. While the importance of skin microbiome makes it an appealing target for promoting skin health, this inherent variability in these communities makes it difficult to identify the underlying molecular mechanisms that link microbiome structure to human fitness. One possible reason for this high level of population diversity is that there is a significant functional redundancy in the population. While a large variety of possible population structures may be functionally equivalent in their aggregate metabolic capacities, the specific assembly of molecular functions would be the key indicator of a microbial community's capacity to influence human host state.

Aging is the accumulation of changes in an organism or object over time. Aging in humans refers to a multidimensional process of physical, biological, psychological, and social change. One of the human organs widely studied within the context of aging is skin. Human skin ages over time, but the specifics of that process, the pace, and extent varies drastically among different individuals, and is a complex interplay between genetic elements, and environmental factors, including microbiome and lifestyle characteristics. Understanding this dynamic is critical for better controlling the aging process.

SUMMARY OF THE INVENTION

The invention relates generally to identifying the specific molecular mechanisms within which microbiome contributes to skin health. To this end, a unique and richly contextualized dataset of skin microbiomes has been assembled for analysis. Using computational biology and machine learning techniques, molecular information from population structure data are extrapolated and the information is used to identify the important links between microbiome and skin health.

Accordingly, in one embodiment, the invention provides a method of identifying the specific molecular mechanisms within which microbiome contributes to skin age. To this end, a unique and richly contextualized dataset of skin microbiomes has been assembled for analysis. Using computational biology and machine learning techniques, molecular information from population structure data are extrapolated and the information is used to identify the important links between microbiome and skin age.

In another embodiment, the invention provides a method of characterizing microbial communities, associated enzymatic activities, and metabolites that can impact skin health and skin age.

In yet another embodiment, the present invention provides a method of identifying microbiome feature targets that influence skin age and interactions with donor parameters like sleep, sun exposure, and antibiotic use.

In still another embodiment, the present invention provides a method for determining a skin age which include analyzing a microbiome of a skin sample from a donor subject and determining the skin age, wherein analyzing includes classifying the microbiome utilizing microbiome taxonomy information.

In another embodiment, the present invention provides a method for determining a customized therapy. The method includes predicting and/or determining a skin age for a subject using the methods of the invention, and prescribing a customized treatment including, but not limited to, oral or topical medications, skin creams, lifestyle recommendations, or a combination thereof, to the subject based on the determined skin age with, or without, the intention of improving overall skin quality.

In yet another embodiment, the present invention provides a method for recommending a lifestyle or product based on a predicted skin age of a subject. The method includes predicting a skin age for a subject using the methods of the invention, and prescribing to the subject one or more lifestyle or product recommendations. In embodiments, the lifestyle or product recommendation is associated with prescription or non-prescription skin care products, sun exposure limits, antibiotic use (e.g., type and quantity), sleep (e.g., daily recommended average hours of sleep, diet, exercise (e.g., type, frequency and/or exertion level), medications, pet ownership (e.g., type of pet), probiotics (e.g., use and type), vitamin and supplement use, or combinations thereof.

In another embodiment, the invention provides a non-transitory computer-readable medium for predicting skin age. The medium includes instructions stored thereon, that when executed on a processor, perform the steps of: a) analyzing microbiome data; and b) generating a predicted skin age.

DETAILED DESCRIPTION OF THE INVENTION

It is now well established that about 100 trillion microorganisms live in and on the human body vastly outnumbering the approximately 10 trillion human cells. These normally harmless viruses, bacteria and fungi are referred to either as commensals (are not harmful to their host) or mutualistic (offer a benefit). Commensal and mutualistic organisms help keep our bodies healthy in many ways: they help us to digest foods and acquire nutrients such as vitamins B and K, encourage our immune system to develop and prevent the colonization of, for example, bacterial pathogens that cause disease by competing with them. Together all of the microorganisms—commensal, mutualistic and pathogenic—are referred to as the body's microbiome and their equilibrium and associated microbiome is closely linked to an individual's health status and vice-versa.

The present invention relates to a combination of experimental and computational workflows that allow characterization of specific molecular mechanisms by which the microbiome contribute to skin health and skin age. A skin profiling platform was used to characterize skin microbiome of multiple individuals at different age groups. Using computational biology and machine learning techniques, molecular information was extrapolated from population structure data and the information was used to identify the important links between microbiome and skin age. In particular, embodiments of the methods and the associated computational platform provided herein relate to collecting a unique and highly contextualized skin microbiome dataset and generating metagenomic predictions and calculating metabolic models from the microbiome community structures. Using these data, computational models were developed for donor age as function of donor parameters and microbiome features. Using this model, microbiome feature targets that influence skin age and interactions with donor parameters like sleep, sun exposure, and antibiotic use were identified. Not only will this lead to specific, microbiome-based hypotheses for intervention for skin health, but also will become a powerful data analysis pipeline for the computational modeling and interpretation of future microbiome data.

The invention provides a method of identifying the specific molecular mechanisms within which microbiome contributes to skin age. To this end, a unique and richly contextualized dataset of skin microbiomes has been assembled for analysis. Using computational biology and machine learning techniques, molecular information from population structure data are extrapolated and the information is used to identify the important links between microbiome and skin age The term "skin" or "subcutaneous tissue" refers to the outer protective covering of the body, consisting of the epidermis (including the stratum corneum) and the underlying dermis, and is understood to include sweat and sebaceous glands, as well as hair follicle structures and nails. Throughout the present application, the adjective "cutaneous" and "subcutaneous" can be used, and should be understood to refer generally to attributes of the skin, as appropriate to the context in which they are used. The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The invention relates generally to using microbiome community structures to predict microbiome metagenomes, the genes and gene abundances present in a microbial community. Predicted metagenomes are comprised of 2055 enzyme functions. From predicted metagenomes, community metabolomes are modeled. Model community metabolomes are comprised of 2893 metabolites, 4481 enzyme function-mediated interactions, and 1346 enzyme functions. From prior experimental result, predicted metagenomes and metabolome correlate well with biological observations.

Figure 1:
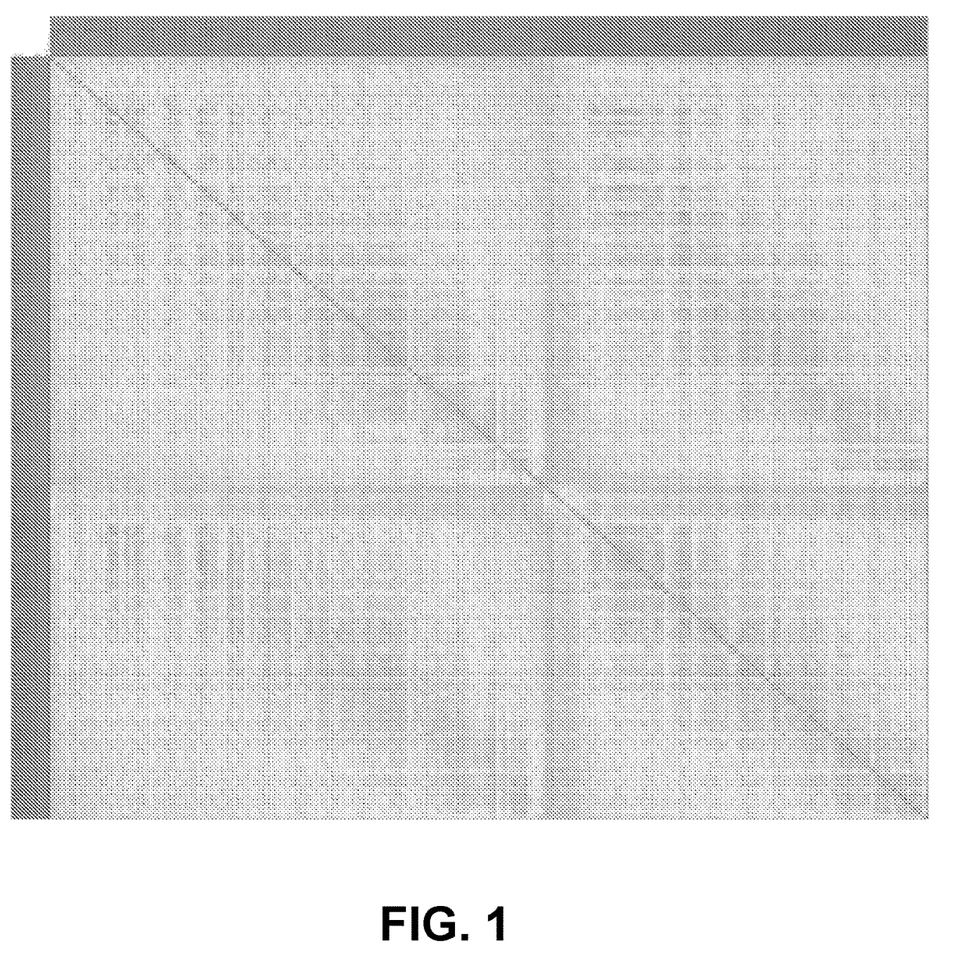
FIG. 1 is a graphical representation of data. Forehead microbiome profiles of multiple individuals were compared using the Bray-Curtis dissimilarity measure. The result was demonstrated as a heat-plot with individual microbiomes segregated to males (in blue) and females (in red) across both rows and columns, sorted in ascending age order. In the heatplot, more similar microbiomes are color-coded in red (dark grey) and less similar examples are shown in green (light grey). The red (grey) halo across the diagonal line proves that age is strong influence on community structure.

To further characterize the association of age with microbiome, the forehead microbiome profiles of multiple individuals were compared using the Bray-Curtis dissimilarity measure. The result was demonstrated as a heat-plot with individual microbiomes segregated to males (in blue) and females (in red), sorted in ascending age order. In the heatplot, more similar microbiomes are color-coded in red and less similar examples are shown in green. The red halo across the diagonal line proves that age is strong influence on community structure.

A machine-learning approach was used to generate computational models that predict donor age as a function of donor parameters (e.g. gender, ethnicity, hours of sleep, hours of sun exposure) and microbiome features (population structure, predicted metagenome). To this end, a statistics-based evolutional algorithm using symbolic regression was used to search the space of mathematical equations to find a model that best fits the data provided, varying both the form and parameters of possible models. Two models were generated. The first used only population structure data for microbiome features, the second incorporated predicted metagenomes and models metabolome in addition to population structure. All the microbiome features, lifestyle information and parameters were collected from human subjects.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Figure 2:
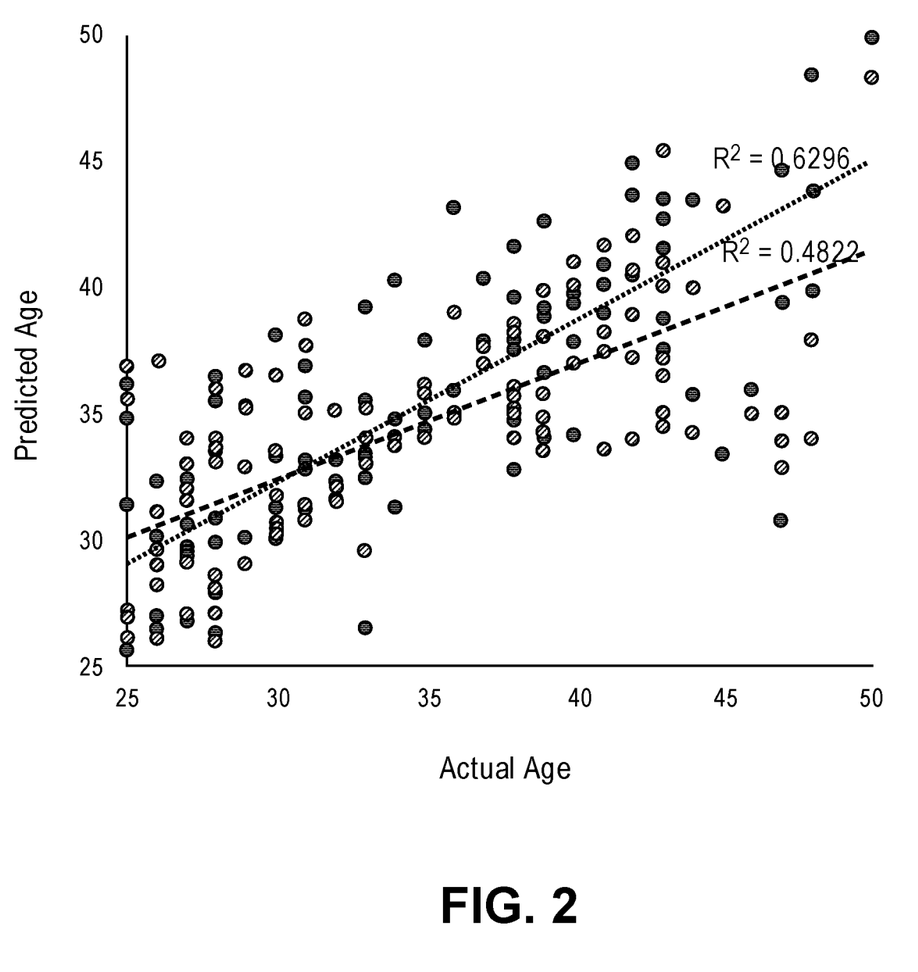
FIG. 2 is a graphical representation of data. Two models were generated to predict skin age based on the microbiome data (i.e. taxa only) or a combination of microbiome plus enzyme activities and metabolites. The taxa only (orange) predicts age correlations with actual age with a $R^2=0.48$. Mixed model (blue) predicts age with greater accuracy and $R^2=0.63$.
Figure 3:
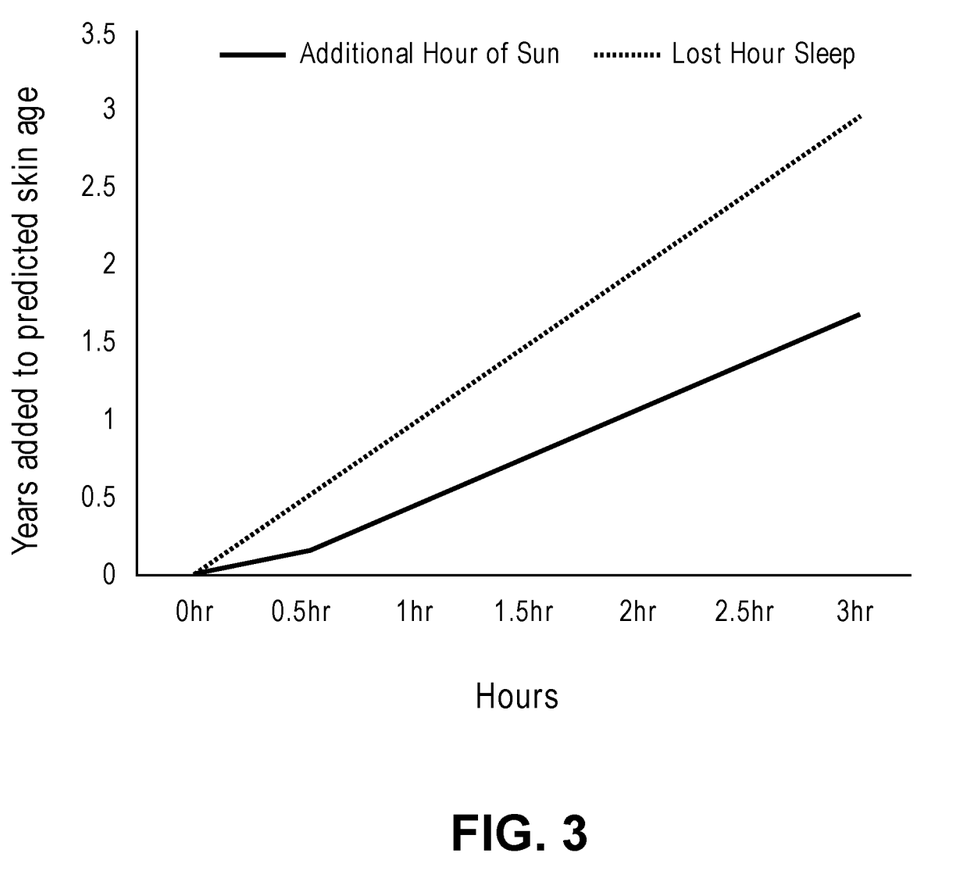
FIG. 3 is a graphical representation of data showing the effect of different environmental factors on skin age. A computational model is built to predict the impact of microbiome and lifestyle parameters on skin age. The generated model can next be used to predict how any lost hour of sleep or extra hour of sun-exposure ages the skin.

Computational models were validated in one of two ways. The first validation method, the correlation between predicted and actual donor age was considered (FIG. 2). Here, the mixed model (Pearson Correlation Coefficient=0.81) outperformed the taxa-only model (Pearson Correlation Coefficient=0.72). While both predictions are strong, the mixed model has the advantage of not only being more accurate, but also the mixed model has the capacity to provide greater insight into the molecular mechanisms than link skin microbiome with skin age. In the second validation method, we predicted the effects of reduced sleep, increasing sun exposure, and use of antibiotics of skin "age" (FIG. 3). As expected, these parameters has a negative effect of predicted skin age. As predicted from computational model, every extra hour of lost sleep "ages" skin ~0.98 years, every extra hour of sun "ages" skin ~0.46 years, and the use of antibiotics "ages" skin ~0.54 years.

Accordingly, in one aspect, the invention provides a method of characterizing the age of skin or subcutaneous tissue of a subject. The method includes: a) obtaining a sample comprising a plurality of microorganisms from the skin or subcutaneous tissue of the subject; and b) analyzing and classifying the plurality of microorganisms of (a) to characterize the microbiome of the subject, thereby characterizing the microbiome of the subject; and c) use the microbiome information to predict skin or subcutaneous tissue age.

As used herein, the terms "sample" and "biological sample" refer to any sample suitable for the methods provided by the present invention. A sample of cells can be any sample, including, for example, a skin or subcutaneous tissue sample obtained by non-invasive techniques such as tape stripping, scraping, swabbing, or more invasive techniques such as biopsy of a subject. In one embodiment, the term "sample" refers to any preparation derived from skin or subcutaneous tissue of a subject. For example, a sample of cells obtained using the non-invasive method described herein can be used to isolate nucleic acid molecules or proteins for the methods of the present invention. Samples for the present invention may be taken from an area of the skin shown to exhibit a disease or disorder, which is suspected of being the result of a disease or a pathological or physiological state, such as psoriasis or dermatitis, or the surrounding margin or tissue. As used herein, "surrounding margin" or "surrounding tissue" refers to tissue of the subject that is adjacent to the skin shown to exhibit a disease or disorder, but otherwise appears to be normal.

Figure 4:
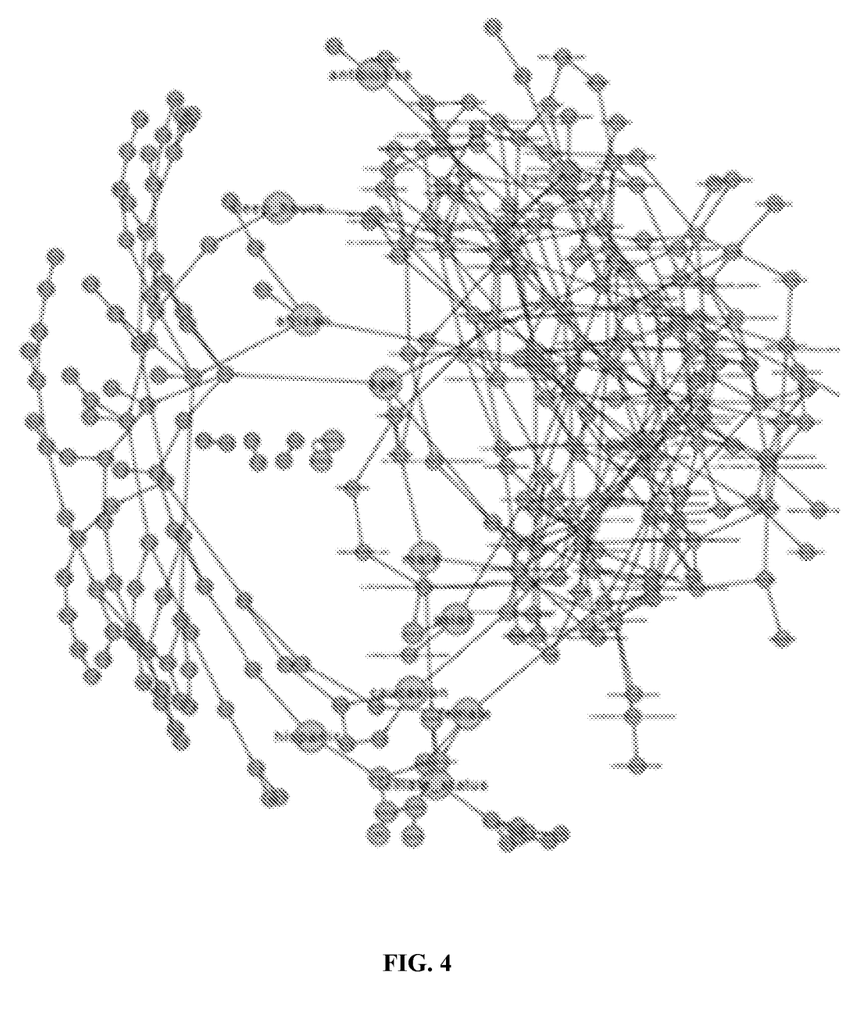
FIG. 4 is a graphical representation of data using Bayesian Network Inference to identify statistically significant casual links between donor parameters and skin microbiome features. In the network figure, donor parameters are shown with grey nodes, bacterial taxa are shown as yellow nodes, enzyme activities are shown as purple nodes and metabolites are shown as blue nodes. All predicted causal relationships between parameters are shown in blue.

Accordingly, in one aspect, the invention proposes a model that describes how the microbiome can potentially protect skin from aging effects. A Baysian Network (BN) model is generated for donor parameters and microbiome features to identify the potential causal links between them. BN are probabilistic graphical models of conditional dependencies between random variables in the form of a directed acyclic graph. Directed edges are relationships between nodes inferred from data such that the state of a child node is dependent on the states of its parent nodes. In the generated network, no node was permitted to be the parent node of a donor parameter. Networks for microbiome taxa, predicted metagenomes, and community metabolomes were generated independently, and then final networks were combined into a composite network (FIG. 4). From this network, a number of potential molecular mechanisms can be predicted, linked to antioxidant activities, antimicrobial activities, and production of anti-inflammatory compounds.

Figure 5:
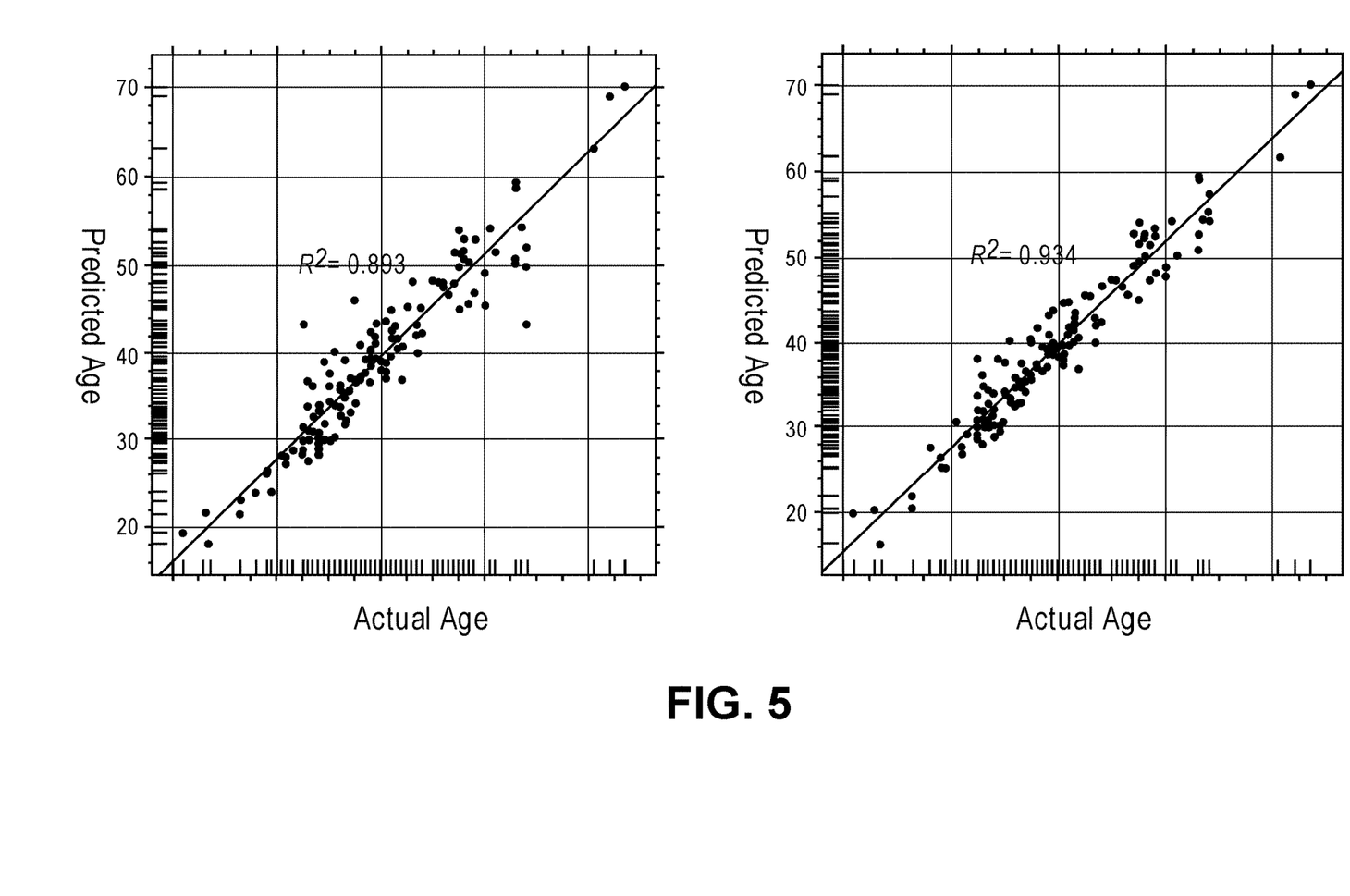
FIG. 5 is a series of graphical representations generated using a random forest model built to predict biological age from skin microbiome alone (left panel) or from a combination of skin microbiome, plus metadata collected from individuals (right panel).

Accordingly, in one aspect, the invention proposes a model that can predict skin age from skin microbiome composition. The model has been built using a random forest approach that can take the microbiome composition as the only input (FIG. 5, left panel) with a R-squared value of 0.89. The model can be improved further by including other metadata including average hours of sun exposure, average hours of sleep, skin microbiome balance, skin microbiome diversity, and skin happiness. The new model which includes the microbiome composition and all above-mentioned metadata (FIG. 5, right panel) has an improved performance with a R-squared value of 0.93.

Figure 6:
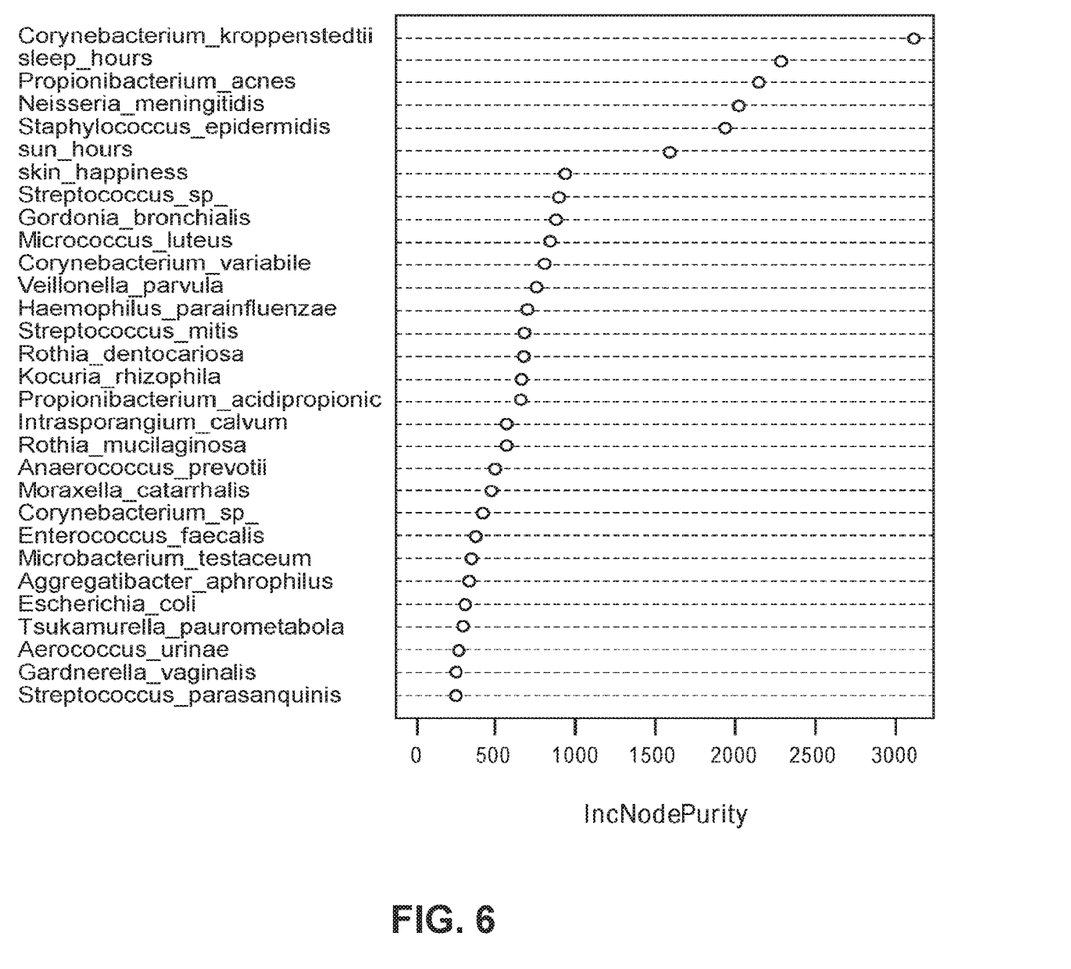
FIG. 6 is a graphical representation showing the importance of different variables deconstructed in the skin age prediction model. The y-axis shows a list of the variables (i.e. microbial species or metadata) and the x-axis is the IncNodePurity, a measure of how impurity changes in a random forest model when variables are randomly permuted.

Contribution of different variables, microbial species, microbial genera, or metadata to skin age can be deconstructed from the model (FIG. 6). The list of variables in the order of their contribution to skin age model are listed in the y-axis from top to bottom. As shown in the graph, *Corynebacterium kroppenstedtii*, hours of sleep, *Propionibacterium*

*acnes, Neisseria meningitides*, and *Staphylococcus epidermidis* are the top variables with maximum contribution to the predicted skin age.

Accordingly, in one aspect, the invention provides a method of characterizing skin age for healthy or disease samples.

As used herein "healthy" refers to a sample from a subject that is free from disease or disorder, a skin disorder, any particular undesirable phenotype or risk thereof. The term healthy skin refers to skin that is devoid of a skin condition, disease or disorder, including, but not limited to inflammation, rash, dermatitis, atopic dermatitis, eczema, psoriasis, dandruff, acne, cellulitis, rosacea, warts, seborrheic keratosis, actinic keratosis, tinea versicolor, viral exantham, shingles, ringworm, and cancer, such as basal cell carcinoma, squamous cell carcinoma, and melanoma.

Additionally, as used herein, a "disease" or "disorder" is intended to generally refer to any skin associated disease, for example, but in no way limited to, inflammation, rash, dermatitis, atopic dermatitis, eczema, psoriasis, dandruff, acne, cellulitis, rosacea, warts, seborrheic keratosis, actinic keratosis, tinea versicolor, viral exantham, shingles, ringworm, and cancer, such as basal cell carcinoma, squamous cell carcinoma, and melanoma.

The term "cancer" as used herein, includes any malignant tumor including, but not limited to, carcinoma, melanoma and sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof. The term "cancerous cell" as provided herein, includes a cell afflicted by any one of the cancerous conditions provided herein. The term "carcinoma" refers to a malignant new growth made up of epithelial cells tending to infiltrate surrounding tissues, and to give rise to metastases. The term "melanoma" refers to a malignant tumor of melanocytes which are found predominantly in skin but also in bowel and the eye. "Melanocytes" refer to cells located in the bottom layer, the basal lamina, of the skin's epidermis and in the middle layer of the eye. Thus, "melanoma metastasis" refers to the spread of melanoma cells to regional lymph nodes and/or distant organs (e.g., liver, brain, breast, prostate, etc.).

The microbiome profiles can be generated by any method and platform that utilizes analysis of a nucleic acid molecule, such as sequencing a nucleic acid molecule. Sequencing methods may include whole genome sequencing, next generation sequencing, Sanger-sequencing, 16S rDNA sequencing and 16S rRNA sequencing. Further, such methods and platforms described herein may utilize mass-spectrometry, quantitative PCR, immunofluorescence, in situ hybridization, a microbial staining based platform, or combination thereof.

In embodiments, the input to the identification platform can be any nucleic acid, including DNA, RNA, cDNA, miRNA, mtDNA, single or double-stranded. This nucleic acid can be of any length, as short as oligos of about 5 bp to as long a megabase or even longer. As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

Micro-RNAs (miRNA) are small single stranded RNA molecules an average of 22 nucleotides long that are involved in regulating mRNA expression in diverse species including humans (reviewed in Bartel 2004). The first report of miRNA was that of the lin-4 gene, discovered in the worm *C. elegans* (Lee, Feinbaum et al. 1993). Since then hundreds of miRNAs have been discovered in flies, plants and mammals. miRNAs regulate gene expression by binding to the 3'-untranslated regions of mRNA and catalyze either i) cleavage of the mRNA; or 2) repression of translation. The regulation of gene expression by miRNAs is central to many biological processes such as cell development, differentiation, communication, and apoptosis (Reinhart, Slack et al. 2000; Baehrecke 2003; Brennecke, Hipfner et al. 2003; Chen, Li et al. 2004). Recently it has been shown that miRNA are active during embryogenesis of the mouse epithelium and play a significant role in skin morphogenesis (Yi, O'Carroll et al. 2006).

Given the role of miRNA in gene expression it is clear that miRNAs will influence, if not completely specify the relative amounts of mRNA in particular cell types and thus determine a particular gene expression profile (i.e., a population of specific mRNAs) in different cell types. In addition, it is likely that the particular distribution of specific miRNAs in a cell will also be distinctive in different cell types. Thus, determination of the miRNA profile of a tissue may be used as a tool for expression profiling of the actual mRNA population in that tissue. Accordingly, miRNA levels and/or detection of miRNA mutations are useful for the purposes of disease detection, diagnosis, prognosis, or treatment-related decisions (i.e., indicate response either before or after a treatment regimen has commenced) or characterization of a particular disease in the subject.

As used herein, the term "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration.

A "probe" or "probe nucleic acid molecule" is a nucleic acid molecule that is at least partially single-stranded, and that is at least partially complementary, or at least partially substantially complementary, to a sequence of interest. A probe can be RNA, DNA, or a combination of both RNA and DNA. It is also within the scope of the present invention to have probe nucleic acid molecules comprising nucleic acids in which the backbone sugar is other that ribose or deoxyribose. Probe nucleic acids can also be peptide nucleic acids. A probe can comprise nucleolytic-activity resistant linkages or detectable labels, and can be operably linked to other moieties, for example a peptide.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

As used herein "hybridization" refers to the process by which a nucleic acid strand joins with a complementary strand through base pairing. Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

As used herein, the term "skin flora" or "microbiome" refers to microorganisms, including bacteria, viruses, and fungi that inhabit the skin or subcutaneous tissues of the subject.

As used herein, the terms microbial, microbe, or microorganism refer to any microscopic organism including prokaryotes or eukaryotes, bacterium, archaebacterium, fungus, virus, or protist, unicellular or multicellular.

As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. Thus, a "treatment regimen" refers to any systematic plan or course for treating a disease or cancer in a subject.

In embodiments, nucleic acid molecules can also be isolated by lysing the cells and cellular material collected from the skin sample by any number of means well known to those skilled in the art. For example, a number of commercial products available for isolating polynucleotides, including but not limited to, RNeasy™ (Qiagen, Valencia, Calif.) and TriReagent™ (Molecular Research Center, Inc, Cincinnati, Ohio) can be used. The isolated polynucleotides can then be tested or assayed for particular nucleic acid sequences, including a polynucleotide encoding a cytokine. Methods of recovering a target nucleic acid molecule within a nucleic acid sample are well known in the art, and can include microarray analysis.

As discussed further herein, nucleic acid molecules may be analyzed in any number of ways known in the art that may assist in determining the microbiome and/or metabolome associated with an individual's skin. For example, the presence of nucleic acid molecules can be detected by DNA-DNA or DNA-RNA hybridization or amplification using probes or fragments of the specific nucleic acid molecule. Nucleic acid amplification based assays involve the use of oligonucleotides or oligomers based on the nucleic acid sequences to detect transformants containing the specific DNA or RNA.

In another embodiment, antibodies that specifically bind the expression products of the nucleic acid molecules of the invention may be used to characterize the skin lesion of the subject. The antibodies may be used with or without modification, and may be labeled by joining them, either covalently or non-covalently, with a reporter molecule.

A wide variety of labels and conjugation techniques are known by those skilled in the art and may be used in various nucleic acid and amino acid assays. Means for producing labeled hybridization or PCR probes for detecting sequences related to the nucleic acid molecules of Tables 1-6 include oligolabeling, nick translation, end-labeling or PCR amplification using a labeled nucleotide. Alternatively, the nucleic acid molecules, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated. In situ PCR may be utilized for the direct localization and visualization of target nucleic acid molecules and may be further useful in correlating expression with histopathological finding.

Means for producing specific hybridization probes for nucleic acid molecules of the invention include the cloning of the nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

The term "skin care product" or "personal care product" refers to skin care products and includes, but is not limited to, cleansing products, shampoo, conditioner, toners or creams, topical ointments and gels, as well as localized (e.g. under eye) gel, all of which may be formulated to contain ingredients specifically designed to shift microbial population to a healthy profile with or without a commensal or mutualistic organism or mixture of commensal or mutualistic organisms in either an active or dormant state. Such skin care products may further include therapeutic agents, vitamins, antioxidants, minerals, skin toning agents, polymers, excipients, surfactants, probiotics or fraction thereof, microorganism or product from the culture thereof, such a bacteria, fungi and the like, either living, dormant or inactive.

"Skin commensal microorganisms" means both prokaryotes and eukaryotes that may colonize (i.e., live and multiply on human skin) or temporarily inhabit human skin in vitro, ex vivo and/or in vivo. Exemplary skin commensal microorganisms include, but are not limited to, Alphaproteobacteria, Betaproteobacteria, Gammaproteobacteria, Propionibacteria, Corynebacteria, Actinobacteria, Clostridiales, Lactobacillales, *Staphylococcus, Bacillus, Micrococcus, Streptococcus*, Bacteroidales, Flavobacteriales, *Enterococcus, Pseudomonas, Malassezia*, Maydida, *Debaroyomyces*, and *Cryptococcus*.

*P. acnes* is a commensal, non-sporulating bacilliform (rod-shaped), gram-positive bacterium found in a variety of locations on the human body including the skin, mouth, urinary tract and areas of the large intestine. *P. acnes* can consume skin oil and produce byproducts such as short-chain fatty acids and propionic acid, which are known to help maintain a healthy skin barrier. Propionibacteria such as *P. acnes* also produce bacteriocins and bacteriocin-like compounds (e.g., propionicin P1G-1, jenseniin G, propionicins SM1, SM2 T1, and acnecin), which are inhibitory toward undesirable lactic acid-producing bacteria, gram-negative bacteria, yeasts, and molds. In embodiments, a subject having skin identified as having *P. acnes* may be treated with a personal care product designed to inhibit growth and proliferation of *P. acnes*.

In an embodiment, the invention provides a method of characterizing skin and/or subcutaneous tissue comprising collecting a sample from a subject containing skin or subcutaneous tissue flora. Skin and subcutaneous tissue flora of healthy individuals can be collected using swiping, scraping, swabbing, using tape strips or any other effective microbial collection method. The harvested sample can be profiled on a NGS, Sanger-sequencing, mass-spectrometry, quantitative PCR, immunofluorescence, in situ hybridization, or microbial staining based platform. For sequencing-based platforms, this can be done either using a whole-genome sequencing approach, or via targeted applications, a prominent example of which is 16S rDNA sequencing. All the above-mentioned identification methods can be implemented on samples directly collected from individuals without any proliferation step. This way, minimal bias is introduced toward identification of a mixture of culturable and unculturable microorganisms. A proprietary analysis algorithm can be used to identify species composition of each individual. A consensus healthy profile may be constructed from the healthy cohort. The healthy profile may be updated real time as more samples are collected over time. The healthy profile will serve as the reference for comparing all individual samples, i.e. profiles. Examples of identified bacteria belong to any phylum, including Actinobacteria, Firmicutes, Proteobacteria, Bacteroidetes. It will typically include common species such as Propionibacteria, Staphylococci, Corynebacteria, and Acenitobacteria species.

In an embodiment, the invention provides a platform or method for characterizing skin and subcutaneous tissue microbial flora of individuals with skin conditions. Skin and subcutaneous tissue flora of individuals with skin conditions that are considered to be suboptimal can be collected using swiping, swabbing, tape strips or any other effective microbial collection method. Collected microbial sample can be profiled on a NGS, Sanger-sequencing, mass-spectrometry, quantitative PCR, immunofluorescence, in situ hybridization, or microbial staining based platform. For the sequencing based platforms, this can be done either using a whole-genome sequencing approach, or via targeted applications, a prominent example of which is 16S rDNA sequencing. All the identification methods can be implemented on samples directly collected from individuals without any proliferation step. This way, minimal bias is introduced toward identification of a mixture of culturable and unculturable microorganisms. A personal skin and subcutaneous tissue flora profile can be generated for each individual. Individuals, based on their phenotypic characteristics, can be placed under specific skin condition categories as well. Such clustering effort will help to identify biological significant patterns which are characteristic of each cohort. The microbial composition of the affected cohort is distinct from the healthy profile. Microbial species which are associated with any given skin condition can be used as early diagnostic markers for individuals who have not developed a visual skin condition but may be prone to that. Examples of identified bacteria belong to any phylum, including Actinobacteria, Firmicutes, Proteobacteria, Bacteroidetes. It will typically include common species, such as Propionibacteria, Staphylococci, Corynebacteria, and Acenitobacteria species. Damaged skin can impact the composition of bacterial flora or can cause nonpathogenic bacteria to become pathogenic.

In an embodiment, the invention provides a platform or method for characterizing a consensus healthy skin and subcutaneous tissue metabolite profile. The metabolome associated with skin and subcutaneous tissue flora can also be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance in a particular disease pathology. All the above-mentioned identification methods can be implemented on samples directly collected from individuals without any proliferation step. This way, minimal bias is introduced in the population composition. A proprietary analysis algorithm may be used to identify metabolite composition of each individual's skin flora. A consensus healthy profile may be constructed from the healthy cohort. The healthy profile may be updated real time as more samples are collected over time. The healthy profile will serve as the reference for comparing all individual samples, i.e. profiles.

In an embodiment, the invention provides a platform or method for characterizing skin and subcutaneous tissue microbial flora of individuals with skin conditions. Metabolite composition of skin and subcutaneous tissue flora of individuals with skin conditions that are considered to be suboptimal can be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance. All the above-mentioned identification methods can be implemented on samples directly collected from individuals without any proliferation step. This way, minimal bias is introduced in the population composition. A personal profile can be generated for each individual that reflects the metabolite composition of the skin and subcutaneous tissue flora. Individuals, based on their phenotypic characteristics, can be placed under specific skin condition categories as well. Such clustering effort will help to identify biological significant patterns that are characteristic of each cohort. The metabolite composition of the affected cohort is distinct from the healthy profile. Metabolites which are associated with any given skin condition can be used as early diagnostic markers for individuals who have not developed a visual skin condition but may be prone to that.

In an embodiment, the platform or method described herein may be provided as a test for profiling the skin flora of any individual, either healthy or with a skin condition and also their associated metabolome. Such test would be sensitive to characterize the dominant skin flora and metabolites of any individual. A customized or personalized evaluation of any individual's flora may be conducted and identified skin and subcutaneous tissue flora and metabolites may be compared to healthy and also affected skin profiles. A customized or personalized report may be generated which will specify species composition of the individual's skin and subcutaneous tissue flora and also its associated metabolites. Such report will enlist the beneficial and commensal species that are depleted or over-represented in each individual. It will also include the list of beneficial or undesired metabolites that are either depleted or over-represented in each individual. This may be used for formulation of the customized or personalized skin care or personal care product. Such report may also form the basis of a recommendation engine that generates clinical, lifestyle and product recommendations that may improve the health of the skin either directly as a result of a change in the diversity or composition of an individual's skin flora, or a change in both diversity and composition of an individual's skin flora. Alternatively, the test can be administered to assess the performance of other skin care and personal care products, therapies, or evaluate any disruption of the normal skin flora or metabolites. The test can be performed before, during, and after any skin treatment in order to monitor the efficacy of that treatment regimen on skin flora or its associated metabolites. The test can also be used for early diagnostic of skin conditions that are associated with a signature microbial profile or their accompanying metabolites. The sensitivity of the test allows early diagnostic of such skin conditions before their phenotypic outbreak. In an aspect, the invention provides a method for generating, or a customized or personalized skin care or personal care product formulated for a particular individual. The customized or personalized product contains one or more beneficial or commensal microorganisms or a set of chemicals and metabolites which may be depleted in any given individual. Regular administration of such skin care products and personal care products should shift the suboptimal profile towards a healthy equilibrium. Skin care product may be applied after cleansing the existing flora with a proprietary lotion that will enhance the efficacy of colonization of skin care product microorganisms or its constituent metabolites. Any customized or personalized skin care or personal care product can contain one or more microorganisms, culturable or unculturable. The customized or personalized product can alternatively be a substrate and nutrients that favor the establishment or proliferation of mutualistic or commensal organisms and/or suppression of pathogenic organisms. Those chemicals and metabolites are either synthesized in vitro or purified from a microorganism.

The present invention is described partly in terms of functional components and various processing steps. Such functional components and processing steps may be realized by any number of components, operations and techniques configured to perform the specified functions and achieve the various results. For example, the present invention may employ various biological samples, biomarkers, elements, materials, computers, data sources, storage systems and media, information gathering techniques and processes, data processing criteria, statistical analyses, regression analyses and the like, which may carry out a variety of functions. In addition, although the invention is described in the medical diagnosis context, the present invention may be practiced in conjunction with any number of applications, environments and data analyses; the systems described herein are merely exemplary applications for the invention.

Methods for data analysis according to various aspects of the present invention may be implemented in any suitable manner, for example using a computer program operating on the computer system. An exemplary analysis system, according to various aspects of the present invention, may be implemented in conjunction with a computer system, for example a conventional computer system comprising a processor and a random access memory, such as a remotely-accessible application server, network server, personal computer or workstation. The computer system also suitably includes additional memory devices or information storage systems, such as a mass storage system and a user interface, for example a conventional monitor, keyboard and tracking device. The computer system may, however, comprise any suitable computer system and associated equipment and may be configured in any suitable manner. In one embodiment, the computer system comprises a stand-alone system. In another embodiment, the computer system is part of a network of computers including a server and a database.

The software required for receiving, processing, and analyzing biomarker information may be implemented in a single device or implemented in a plurality of devices. The software may be accessible via a network such that storage and processing of information takes place remotely with respect to users. The analysis system according to various aspects of the present invention and its various elements provide functions and operations to facilitate microbiome analysis, such as data gathering, processing, analysis, reporting and/or diagnosis. The present analysis system maintains information relating to microbiomes and samples and facilitates analysis and/or diagnosis, For example, in the present embodiment, the computer system executes the computer program, which may receive, store, search, analyze, and report information relating to the microbiome. The computer program may comprise multiple modules performing various functions or operations, such as a processing module for processing raw data and generating supplemental data and an analysis module for analyzing raw data and supplemental data to generate a models and/or predictions.

The epigenetic analysis system may also provide various additional modules and/or individual functions. For example, the epigenetic analysis system may also include a reporting function, for example to provide information relating to the processing and analysis functions. The epigenetic analysis system may also provide various administrative and management functions, such as controlling access and performing other administrative functions.

Although the invention has been described with reference to the above examples, it will be understood that modifications and variations are encompassed within the spirit and scope of the invention. Accordingly, the invention is limited only by the following claims.

What is claimed is:

1. A method for determining a skin age of an individual and improving an overall skin quality of the individual, comprising:
   (a) analyzing a microbiome of a skin sample from the individual, wherein analyzing comprises classifying the microbiome utilizing microbiome taxonomy information, thereby determining a microbiome classification;
   (b) receiving a parameter comprising lifestyle information of the individual, a gender of the individual, an ethnicity of the individual, a duration of sleep of the individual, a duration of sun exposure of the individual, a diet of the individual, an antibiotic used by the individual, or a skin care product used by the individual;
   (c) determining the skin age of the individual based on the microbiome classification using a computer-implemented model that models relationships of population skin ages, population microbiome classifications, and population parameters comprising population lifestyle information, population genders, population ethnicities, population durations of sleep, population durations of sun exposure, population diets, population antibiotics, or population skin care products;
   (d) determining, based on the skin age of the individual, a skin care product not used by the individual and a parameter modification comprising a modification of the duration of sleep of the individual, a modification of the duration of sun exposure of the individual, a modification of the diet of the individual, a modification of the antibiotic used by the individual, or a modification of the skin care product used by the individual, wherein the skin care product not used by the individual and the parameter modification will improve the skin age of the individual and thereby improve the overall skin quality of the individual; and
   (e) treating the individual with the skin care product not used by the individual, the parameter modification, or a combination thereof.

2. The method of claim 1, wherein classifying further utilizes a microbiome feature comprising a population structure, an enzymatic function, a metabolome, or a proteome of the microbiome.

3. The method of claim 1, wherein analyzing and/or classifying comprises a computer-implemented computation method utilizing a mathematical algorithm.

4. The method of claim 1, further comprising providing a data analysis pipeline for computational modeling and interpretation of microbiome data.

5. The method of claim 1, wherein the skin sample is obtained from a skin or subcutaneous tissue of the individual via swipe, scrape, swab, biopsy, or tape.

6. The method of claim 1, wherein the microbiome comprises a plurality of microorganisms selected from the group consisting of bacteria, fungi and combinations thereof.

7. The method of claim 1, wherein the microbiome comprises one or more bacteria or fungi selected from the group consisting of Alphaproteobacteria, Betaproteobacteria, Gammaproteobacteria, Propionibacteria, Proteobacteria, Bacteroidetes, Corynebacteria, Actinobacteria, Clostridiales, Lactobacillales, *Staphylococcus, Bacillus, Micrococcus, Streptococcus*, Bacteroidales, Flavobacteriales, Firmicutes, *Enterococcus, Pseudomonas, Malassezia*, Maydida, *Debaroyomyces*, and *Cryptococcus*.

8. The method of claim 1, wherein the microbiome comprises a bacteria of the genus Propionibacteria, Staphylococci, Corynebacteria, or Acenitobacteria.

9. The method of claim 1, wherein the microbiome comprises a bacteria selected from the group consisting of *Propionibacterium acnes, Corynebacterium kroppenstedtii, Neisseria meningitides*, and *Staphylococcus epidermidis*.

10. The method of claim 1, wherein analyzing comprises sequencing a nucleic acid.

11. The method of claim 10, wherein sequencing is selected from whole genome sequencing, next generation sequencing, Sanger-sequencing, 16S rDNA sequencing and 16S rRNA sequencing.

12. The method of claim 1, comprising repeating steps (a) through (e).

* * * * *